(12) United States Patent
Hwang et al.

(10) Patent No.: US 9,459,227 B2
(45) Date of Patent: Oct. 4, 2016

(54) PORTABLE DIAGNOSTIC TEST APPARATUS

(71) Applicant: SAMSUNG ELECTRONICS CO., LTD., Suwon-si (KR)

(72) Inventors: In Duk Hwang, Incheon (KR); Yeon Moo Chung, Seoul (KR); Na Hui Kim, Hwaseong-si (KR); Jeong Je Park, Hwaseong-si (KR); Chul Ho Yun, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/244,421

(22) Filed: Apr. 3, 2014

(65) Prior Publication Data

US 2015/0072406 A1 Mar. 12, 2015

(30) Foreign Application Priority Data

Sep. 11, 2013 (KR) ........................ 10-2013-0109190

(51) Int. Cl.
*G01N 33/00* (2006.01)
*G01N 27/26* (2006.01)
*G01N 21/78* (2006.01)
(Continued)

(52) U.S. Cl.
CPC ............. *G01N 27/26* (2013.01); *A61B 5/1405* (2013.01); *A61B 5/14532* (2013.01); *A61B 5/157* (2013.01); *A61B 5/150022* (2013.01); *A61B 5/15186* (2013.01); *A61B 5/150305* (2013.01); *A61B 5/150358* (2013.01); *G01N 21/78* (2013.01); *G01N 33/4875* (2013.01); *G01N 33/5438* (2013.01); *A61B 5/1455* (2013.01);

(Continued)

(58) Field of Classification Search
CPC .... G01N 27/26; G01N 21/78; A61B 5/1405; A61B 5/157
See application file for complete search history.

(56) References Cited

U.S. PATENT DOCUMENTS

| 6,602,469 | B1 | 8/2003 | Maus et al. | |
|---|---|---|---|---|
| 7,424,437 | B2 * | 9/2008 | Maus et al. | ...................... 705/2 |
| 2006/0040333 | A1 | 2/2006 | Zocchi | |

FOREIGN PATENT DOCUMENTS

| DE | 202005005375 U1 | 9/2005 |
|---|---|---|
| DE | 102004057503 A1 | 6/2006 |

(Continued)

OTHER PUBLICATIONS

Communication dated Sep. 3, 2015, issued by the European Patent Office in counterpart European Application No. 14184399.5.

(Continued)

*Primary Examiner* — Sam P Siefke
(74) *Attorney, Agent, or Firm* — Sughrue Mion, PLLC

(57) ABSTRACT

Provided is a portable diagnostic test apparatus including: an accommodation portion including an outer side, an inner side, and an accommodation space provided on the inner side; a hinge; and a main body coupled to the accommodation portion by the hinge, where the portable diagnostic test apparatus is configured to be opened and closed by rotating one of the accommodation portion and the main body about the hinge, and where the main body is configured to obtain a result of a measurement based on data collected from drawn blood. The main body and/or the accommodation portion includes at least one strip keeping portion configured to store at least one strip. The at least one strip keeping portion may include: a housing; a discharge portion; and a first movement portion configured to move one of the strips to the discharge portion.

15 Claims, 22 Drawing Sheets

(51) Int. Cl.
*A61B 5/15* (2006.01)
*A61B 5/145* (2006.01)
*A61B 5/151* (2006.01)
*A61B 5/157* (2006.01)
*G01N 33/487* (2006.01)
*G01N 33/543* (2006.01)
*A61B 5/1455* (2006.01)

(52) U.S. Cl.
CPC ...... *A61B 5/14546* (2013.01); *A61B 5/150717* (2013.01); *A61B 2562/0295* (2013.01)

(56) References Cited

FOREIGN PATENT DOCUMENTS

| | | |
|---|---|---|
| EP | 2315012 A2 | 4/2011 |
| WO | 2006065754 A2 | 6/2006 |
| WO | 2008111933 A1 | 9/2008 |

OTHER PUBLICATIONS

Communication issued on Jan. 16, 2015 by the European Patent Department in related application No. 14184399.5.

* cited by examiner

PORTABLE DIAGNOSTIC TEST APPARATUS

CROSS-REFERENCE TO RELATED APPLICATION

This application claims priority from Korean Patent Application No. 10-2013-109190, filed on Sep. 11, 2013 in the Korean Intellectual Property Office, the disclosure of which is incorporated herein by reference in its entirety.

BACKGROUND

1. Field

Apparatuses consistent with exemplary embodiments relate to a portable diagnostic test apparatus.

2. Description of the Related Art

Drawing blood generally refers to a technique of drawing blood from a person or an animal and collecting the blood for the purpose of diagnosing potential diseases of the person or the animal. Drawing blood may be performed by collecting a small amount of blood from a capillary vessel (a small amount of blood drawing) or by collecting blood directly from veins or arteries (a large amount of blood drawing). In the case of a small amount of blood drawing, a wound may be made at an end of a finger or an ear lobe using a knife, a lancet, or various types of needles for drawing blood, and then blood ejected from the wound may be collected. In the case of a large amount of blood drawing, a tubular needle having a central hollow may be inserted directly into veins or arteries, and then blood may be extracted using an atmospheric pressure and may be collected. Blood collected through the technique of drawing blood is analyzed to measure blood sugar, blood cholesterol, or neutral fats so that the health or a disease of the person or the animal can be checked.

In this case, a predetermined diagnostic test apparatus may be used to analyze the collected blood. For example, a blood-sugar testing device may be used to measure a blood-sugar amount, and a hyperlipidemia diagnostic device may be used to measure cholesterol or neutral fats.

The blood-sugar testing device is a measuring device for measuring a concentration value of glucose in the blood from the collected blood, for example, a device for measuring a blood-sugar amount of a patient's blood injected into a strip that reacts with the patient's blood. In general, the blood-sugar testing device measures a blood-sugar amount using photometry or an electrochemical measurement. In the case of photometry, a blood-sugar amount is measured by sensing discoloration that occurs when glucose reacts with enzymes. In the case of electrochemical measurement, a concentration of glucose in the blood is measured based on a voltage or current signal generated according to electrons which are generated when glucose reacts with enzymes.

SUMMARY

One or more exemplary embodiments provide a diagnostic test apparatus that is capable of being conveniently used and maintained and has high portability.

One or more exemplary embodiments also provide a portable diagnostic test apparatus that is capable of measuring and/or diagnosing a plurality of objects to be measured, for example, blood sugar, cholesterol, or neutral fats, using one device.

In accordance with an aspect of an exemplary embodiment, there is provided a portable diagnostic test apparatus including: an accommodation portion including an outer side, an inner side, and an accommodation space formed on the inner side; a hinge; and a main body coupled to the accommodation portion by the hinge, wherein the portable diagnostic test apparatus is configured to be opened and closed by rotating one of the accommodation portion and the main body about the hinge, and wherein the main body is configured to obtain a result of a measurement based on data collected from drawn blood.

The accommodation space comprises at least one of a blood drawing device accommodation portion configured to store at least one blood drawing device, and a blood drawing needle accommodation portion configured to store at least one drawing needle.

The main body may be configured to obtain a result of a measurement regarding at least one of blood sugar, cholesterol, and neutral fats based on the data collected from the drawn blood.

The main body may be configured to obtain the result of the measurement using at least one of an electrochemical measurement method, an enzyme color reaction detection method, and a photometry method.

The main body may include a display panel configured to display the result of the measurement. The display panel may include a touch screen panel. The touch screen panel may be configured to display a graphic user interface (GUI) for controlling the main body.

The main body and/or the accommodation portion may include at least one strip keeping portion configured to store at least one strip. The main body and/or the accommodation portion comprise at least one outlet through which the at least one strip may be configured to be ejected when the at least one strip is discharged from the at least one strip keeping portion. The main body and/or the accommodation portion may include an ejection button configured to eject the at least one strip.

The at least one strip keeping portion may include: a housing configured to house a stack of a plurality of the at least one strips; a discharge portion formed on at least one side surface of the housing and configured to sequentially discharge the plurality of the at least one strips; and a first movement portion configured to move one of the plurality of the at least one strips to the discharge portion.

The portable diagnostic test apparatus may further include at least one outlet provided on at least one of the main body and the accommodation portion, wherein each of the plurality of the at least one strips sequentially discharged through the discharge portion may be configured to be ejected through the at least one outlet.

The first movement portion may be configured to push the plurality of the at least one strips in a stacked order and may be configured to move the plurality of the at least one strips to the discharge portion so that one of the plurality of the at least one strips is positioned to be discharged through the discharge portion.

The first movement portion may be configured to push one strip among the plurality of the at least one strips stacked on the housing and may be configured to move the one strip to the discharge portion so that the one strip is positioned to be discharged through the discharge portion.

The first movement portion may be configured to push a strip disposed at the uppermost end or the lowermost end among the plurality of the at least one strips stacked in the housing so that the strip is positioned to be discharged through the discharge portion. The at least one strip keeping portion may further include a second movement portion configured to move the plurality of the at least ones strip inside the housing downwards or upwards after one of the at least one strips is discharged through the discharge portion.

The housing may include a guide portion configured to guide movement of the first movement portion.

Each of the plurality of the at least one strips may respectively include a first electrode, and the at least one strip keeping portion may further include at least one second electrode configured to contact the first electrodes.

The at least one strip keeping portion may further include at least one elastic body configured to apply an elastic force to the first movement portion.

In accordance with another exemplary embodiment, a portable diagnostic test apparatus includes: an accommodation portion including an outer side, an inner side, and an accommodation space formed on the inner side; and a main body configured to open and close the accommodation portion and configured to obtain a result of a measurement based on data collected from drawn blood, wherein at least one of the accommodation portion and the main body includes at least one strip keeping portion configured to store at least one strip, and at least one outlet through which the at least one strip is configured to be ejected after being discharged from the at least one strip keeping portion.

The portable diagnostic test apparatus may further include a hinge portion that hinge-couples the main body and the accommodation portion. The portable diagnostic test apparatus may further include at least one sliding portion that couples the main body and the accommodation portion by a sliding motion and at least one pivot member that couples the main body and the accommodation portion to each other. When the portable diagnostic test apparatus includes the pivot member, the main body may be rotated around the at least one pivot member to thereby open and close the accommodation portion.

The accommodation space may include at least one of a blood drawing device accommodation portion configured to store at least one blood drawing device and a blood drawing needle accommodation portion configured to store at least one blood drawing needle. At least one of the main body and the accommodation portion may include an ejection button configured to eject the at least one strip.

The at least one strip keeping portion may include: a housing configured to stack a plurality of the at least one strips; a discharge portion formed on at least one side surface of the housing and configured to sequentially discharge the plurality of the at least one strips; and a first movement portion configured to move the plurality of the at least one strips to the discharge portion.

The portable diagnostic test apparatus may further include at least one outlet provided on at least one of the main body and the accommodation portion, wherein each of the plurality of the at least one strips sequentially discharged through the discharge portion may be configured to be ejected through the at least one outlet.

The first movement portion may be configured to push the plurality of the at least one strips in a stacked order and may be configured to move the plurality of the at least one strips to the discharge portion so that one of the plurality of the at least one strips is positioned to be discharged through the discharge portion. The first movement portion may be configured to push one strip among the plurality of the at least one strips stacked on the housing and may be configured to move the one strip to the discharge portion so that the one strip is positioned to be discharged through the discharge portion. The first movement portion may be configured to push a strip disposed at an uppermost end or a lowermost end among the plurality of the at least one strips stacked on the housing so that the strip is configured to be discharged through the discharge portion.

The at least one strip keeping portion may further include a second movement portion configured to move the plurality of the at least one strips inside the housing downwards or upwards after one of the at least one plurality of the strips is discharged through the discharge portion.

The housing may include a guide portion configured to guide movement of the first movement portion.

Each of the plurality of the at least one strips may respectively include a first electrode, and the at least one strip keeping portion may further include at least one second electrode configured to contact the first electrodes.

The at least one strip keeping portion may further include at least one elastic body configured to apply an elastic force to the first movement portion.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1:
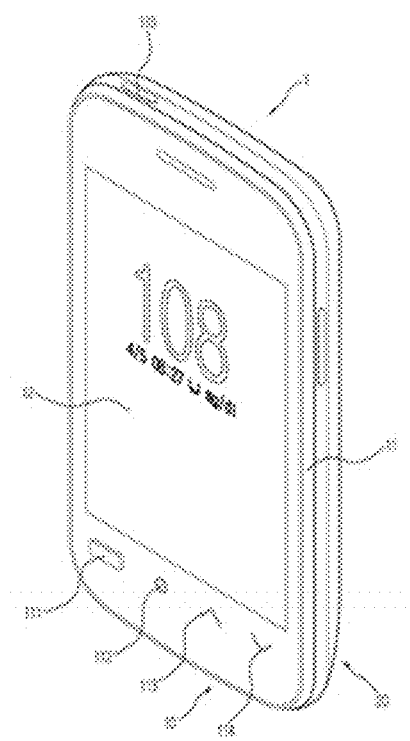
FIG. 1 is a perspective view of a portable diagnostic test apparatus in accordance with an exemplary embodiment.

Reference will now be made in detail to the exemplary embodiments, examples of which are illustrated in the accompanying drawings, wherein like reference numerals refer to like elements throughout.

Figure 2:
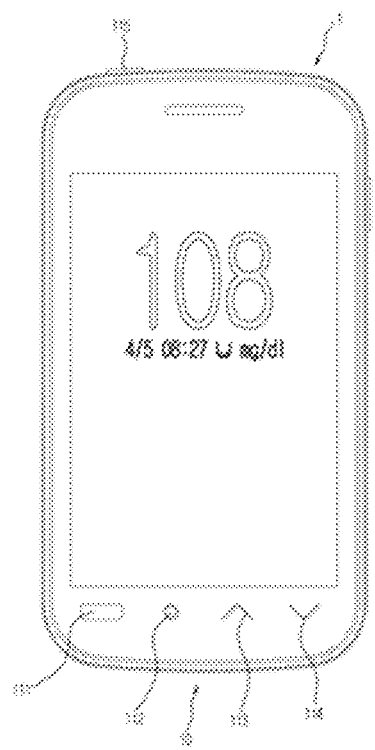
FIG. 2 is a front view of the portable diagnostic test apparatus illustrated in FIG. 1.
Figure 3:
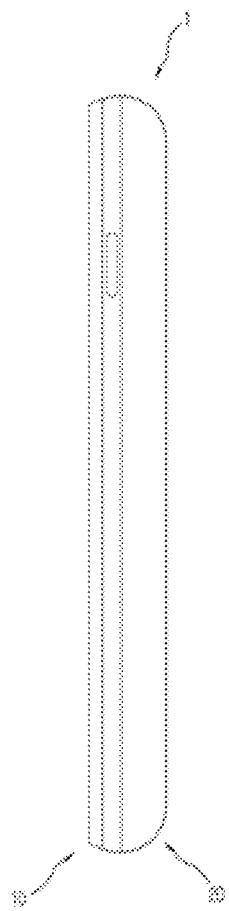
FIG. 3 is a side view of the portable diagnostic test apparatus of FIG. 1.
Figure 4A:
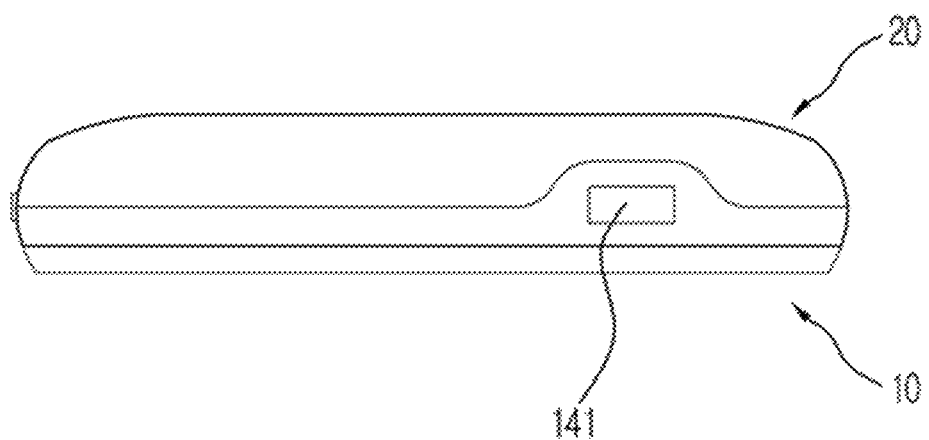
FIGS. 4A and 4B are bottom views of the portable diagnostic test apparatus of FIG. 1.
Figure 4B:
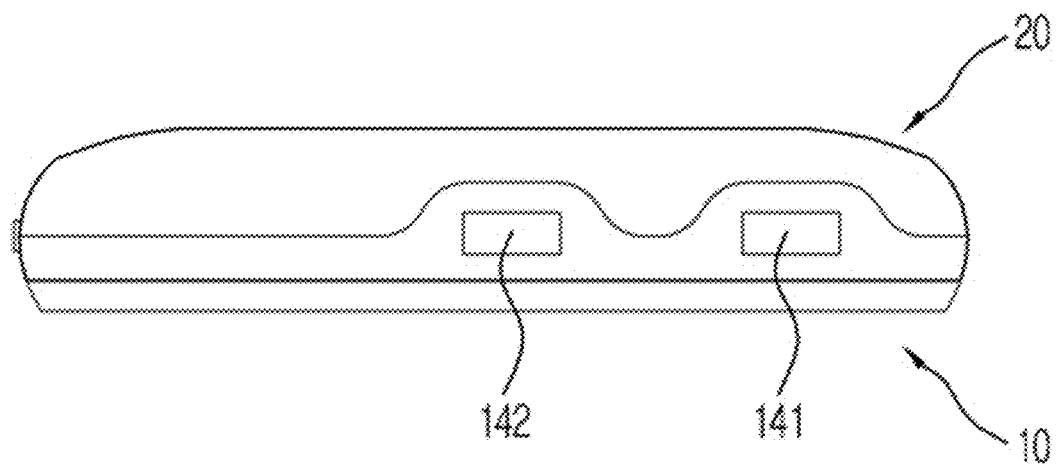

FIG. 1 is a perspective view of a portable diagnostic test apparatus in accordance with an exemplary embodiment, FIG. 2 is a front view of the portable diagnostic test apparatus illustrated in FIG. 1, FIG. 3 is a side view of the portable diagnostic test apparatus of FIG. 1, and FIGS. 4A and 4B are bottom views of the portable diagnostic test apparatus of FIG. 1.

As illustrated in FIGS. 1 through 4B, a portable diagnostic test apparatus 1 in accordance with an exemplary embodiment may include a main body 10 and an accommodation portion 20.

In accordance with an exemplary embodiment, the main body 10 may obtain the result of measurement based on data collected from drawn blood. In detail, the main body 10 may measure blood sugar, blood cholesterol concentration, or neutral fat concentration based on the data collected from the drawn blood, and a processor that obtains the result of the measurement, such as a micro controller unit (MCU), may be installed inside the main body 10. According to an exemplary embodiment, the processor of the main body 10 may obtain the result of the measurement according to at least one of an electrochemical measurement method, an enzyme color reaction detection method, and a photometry method.

Referring to FIGS. 1 and 2, the main body 10 may include a display unit 12 on which an image is displayed, and input units 111 through 114 for receiving instructions or commands from a user.

The display unit 12 may be formed on a front side of the main body 10 for a user's convenience and may display various information required for the user. The display unit 12 may be implemented as a liquid crystal display (LCD) panel, a plasma display panel (PDP), or an organic light emitting diode (OLED) panel, for example. In addition, various display members that may display a predetermined symbol or image may be used to implement the display unit 12.

In detail, the display unit 12 may display the result of the measurement obtained by the main body 10 based on the data collected from the drawn blood. The result of the measurement may be blood sugar, blood cholesterol, or blood neutral fats. Also, the result of the measurement may be blood alcohol concentration (BAC). The display unit 12 may display a measured value in units of mg/dl or mmol.

Also, the display unit 12 may further display various information or instructions required for the user. For example, the display 12 may display a method of using the portable diagnostic test apparatus 1 or may display various procedures or methods required for drawing blood or taking a measurement using collected blood. Also, the display unit 12 may display the result of a diagnosis corresponding to the result of the measurement or may display a coping method required for the user.

The display unit 12 may display the result of the measurement in a monochromatic or polychromatic manner, as various types of information or instructions in accordance with exemplary embodiments.

In accordance with an exemplary embodiment, the input units 111 through 114 may be formed at a lower end of the display unit 12, and the input units 111 through 114 may be implemented as various types of buttons, for example. The input units, for example, various buttons 111 through 114, may output predetermined electrical signals according to a user's manipulation and may transmit the predetermined electrical signals to a central processing unit installed inside the main body 10, such as an MCU, so that the portable diagnostic test apparatus 10 can receive instructions or commands from the user.

According to an exemplary embodiment, the buttons of the input units 111 through 114 may include at least one ejection button 111 or at least one manipulation button 112 through 114, for example. It is understood that the buttons may be arranged in many different combinations.

The ejection button 111 may receive at least one strip ejection instruction. In detail, if the ejection button 111 is manipulated by being pressed by the user, at least one strip may be ejected from at least one strip keeping portion (see 15 of FIG. 7) installed inside the main body 10 through an outlet 141. In accordance with an exemplary embodiment, when the ejection button 111 is manipulated, the portable diagnostic test apparatus 1 may be converted from a standby mode to an active mode, thereby starting measurement or preparation for measurement.

If there are a plurality of outlets 141 and 142, as illustrated in FIG. 4B, a plurality of ejection buttons 111 corresponding in number (e.g., 2) to the plurality of outlets 141 and 142 may be formed at the main body 10.

The manipulation buttons 112 through 114 may receive various instructions or commands required for diagnosis from the user. For example, the manipulation buttons 112 through 114 may receive data or commands which may control various settings to be used for measurement and diagnosis from the user. The manipulation buttons 112 through 114 may receive commands for instructing the starting of measurement or preparation for measurement. Also, for example, the user may manipulate the manipulation buttons 112 through 114, so as to control brightness or contrast of a screen displayed on the display unit 12. If the portable diagnostic test apparatus 1 outputs a measurement step in progress or the result of measurement as voice, for example, the user may also control the size of the volume of voice output through the manipulation buttons 112 through 114. In addition, the manipulation buttons 112 through 114 may receive various instructions or commands to be used for the portable diagnostic test apparatus 1 from the user.

Functions to be performed according to manipulations of the manipulation buttons 112 through 114 may be preset by a designer of the portable diagnostic test apparatus 1 or may be arbitrarily set by the user. Also, even when the same manipulation buttons 112 through 114 are manipulated, different functions may be performed according to an operating state of the portable diagnostic test apparatus 1.

FIGS. 1 and 2 illustrate an example in which the ejection button 111 and manipulation buttons 112 through 114 are formed on the main body 10. However, the ejection button 111 and manipulation buttons 112 through 114 are not limited to being formed at positions on the main body 10, and the ejection button 111 and manipulation buttons 112 through 114 may alternatively be formed, for example, at the accommodation portion 20.

The accommodation portion 20 may be coupled to a rear side of the main body 10, as illustrated in FIGS. 1 and 3. According to an exemplary embodiment, the main body 10 may function as a cover that opens and closes the accommodation portion 20 in a predetermined manner.

The main body 10 and the accommodation portion 20 may be coupled to each other using at least one hinge, using a sliding module, or using a pivot member in accordance with exemplary embodiments. The main body 10 may open and close the accommodation portion 20 using the hinge, the sliding module, or the pivot member.

Also, the main body 10 and the accommodation portion 20 may be coupled to each other using a fastener that may be detachably formed on the main body 10 and/or on the accommodation portion 20, such as a groove or a protrusion. By detaching and reattaching the main body 10 and the accommodation portion 20, the accommodation portion 20 may be opened and closed.

An accommodation space may be formed at an inner side of the accommodation portion 20. Various diagnostic instruments may be accommodated in the accommodation space. According to an exemplary embodiment, various diagnostic instruments may include various instruments required for drawing blood or taking a measurement, such as a knife, a blood drawing device, and various blood drawing needles. The accommodation space in which various diagnostic instruments may be accommodated is formed in the accommodation portion 20 so that the user can reduce the risk of losing various diagnostic instruments and simultaneously can easily carry diagnostic instruments.

The accommodation portion 20 may be opened and closed according to the user's manipulation of the main body 10 or the accommodation portion 20, as described above. Also, both the main body 10 and the accommodation portion 20 may be manipulated such that the accommodation portion 20 can be opened and closed.

Although not shown, in accordance with an exemplary embodiment, at least one of the main body 10 and the accommodation portion 20 may further include an optical signal measurement module for sensing a change in color formation of a strip 30 according to a reagent reaction. The optical signal measurement module may include a light source for outputting predetermined light and a sensing unit for sensing light radiated from the light source. In accordance with an exemplary embodiment, both the light source and the sensing unit may be installed on the main body 10 or the accommodation portion 20, one of the light source and the sensing unit may be installed on the main body 10, and the other one thereof may be installed on the accommodation portion 20. According to an exemplary embodiment, the sensing unit may be installed at a position in which light radiated from the light source and transmitted by the strip 30 or light reflected from the strip 30 can be easily sensed.

If the strip 30 kept in a strip keeping portion 15 is a strip configured to use a photometry method, a reaction part of the strip 30 may be colored or discolored according to glucose or cholesterol concentration in blood injected into the strip 30. The light source of the optical signal measurement module during measurement may radiate predetermined light onto the colored or discolored reaction part, and the sensing unit may sense light transmitted by the reaction part or reflected from the reaction part so as to sense a change in color.

Thus, blood glucose contents in the blood can be measured according to photometry.

As illustrated in FIG. 1, the main body 10 may include a side frame 11 that is installed at an edge of the main body 10 so as to protect the main body 10. The side frame 11 may be formed out of many different types of materials, for example, a metal material, a plastic, a rubber material having elasticity, or a combination thereof.

A power button 115 or an auxiliary button 116 may be formed on the side frame 11 of the main body 10. If the power button 115 is manipulated, power is supplied to various components inside the main body 10, for example, a central processing unit or a memory device, so that the main body 10 can start being driven. The power button 115 may function as a manipulation unit for converting the main body 10 from a stand-by mode to an active mode in accordance with exemplary embodiments.

Referring to FIGS. 4A and 4B, at least one outlet 141 and 142 may be formed at a lower end of the main body 10. The outlets 141 and 142 may eject at least one strip discharged from at least one strip keeping portion 15.

If there are two outlets 141 and 142, as illustrated in FIG. 4B, strips ejected from each outlet 141 may be different types of strips. For example, a strip used in an electrochemical measurement method may be ejected from the first outlet 141 of FIG. 4B, and a strip used in an optical measurement method (e.g., photometry) may be ejected from the other outlet, i.e., the second outlet 142 of FIG. 4B.

In this case, the strip keeping portion 15 that keeps at least one strip may be installed on one of the main body 10 and the accommodation portion 20 or on both the main body 10 and the accommodation portion 20.

If there are two outlets 141 and 142, as illustrated in FIG. 4B, two strip keeping portions 15 may be formed to correspond to the outlets 141 and 142. The strip keeping portions 15 corresponding to the outlets 141 and 142 may keep different strips in accordance with exemplary embodiments. For example, a strip keeping portion corresponding to the first outlet 141 may eject a strip used in the electrochemical measurement method, and a strip keeping portion corresponding to the second outlet 142 may keep a strip used in the photometry method.

The user may select one strip among the strips which are configured to measure blood contents using different techniques and may enable the selected strip to be ejected from the outlets 141 and 142, thereby selectively performing different types of measurement.

Of course, if the portable diagnostic test apparatus 1 only includes one outlet 141, as illustrated in FIG. 4A, a plurality of strip keeping portions 15 may be formed. In this case, each strip keeping portion 15 may keep different types of strips, and a strip kept in one strip keeping portion 15 among the plurality of strip keeping portions 15 may be ejected through one outlet 141 according to the user's selection.

FIGS. 4A and 4B illustrate an example in which one or two outlets 141 and 142 are formed on the main body 10. However, the number of outlets 141 and 142 that may be formed on the main body 10 is not limited thereto, and three or more outlets may be formed on the main body 10 as needed. In this case, a number of strip keeping portions 15 in which at least one strip configured to be ejected through the outlets 141 and 142 is kept, and which correspond to the number of the outlets 141 and 142, may be installed on a portion of the portable diagnostic test apparatus 1, for example, at the main body 10 or the accommodation portion 20. Of course, according to exemplary embodiments, a larger number of strip keeping portions 15 than the number of outlets 141 may be installed on the portable diagnostic test apparatus 1, and alternatively, a smaller number of strip keeping portions 15 than the number of outlets 141 may be installed on the portable diagnostic test apparatus 1.

Also, FIG. 4 illustrates an example in which the outlet 141 is formed on the main body 10. However, exemplary embodiments are not limited thereto. Alternatively, the outlet 141 may be formed on other portions of the portable diagnostic test apparatus 1 as well as the main body 10, for example, on the accommodation portion 20. If the outlet 141 is formed on the accommodation portion 20, the strip keeping portion 15 in which at least one strip configured to be discharged through the outlet 141 is kept may also be formed on the accommodation portion 20. However, the position of the strip keeping portion 15 is not limited thereto, and the strip keeping portion 15 may be installed on the main body 10, on both the main body 10 and the accommodation portion 20, or in other positions altogether.

Also, the outlet 141 may be installed on both the main body 10 and the accommodation portion 20.

Herein after, the main body 10 of the portable diagnostic test apparatus 1 of FIG. 1 will be described in more detail with reference to FIGS. 5 and 6.

Figure 5:
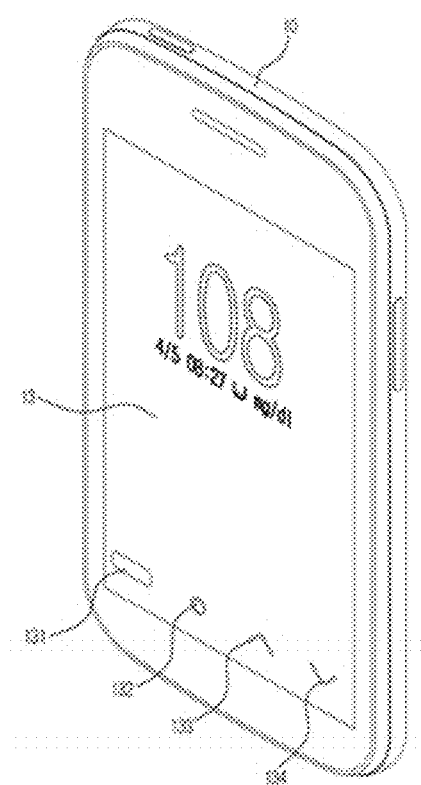
FIG. 5 is a front view of a main body of the portable diagnostic test apparatus of FIG. 1, in accordance with an exemplary embodiment.
Figure 6:
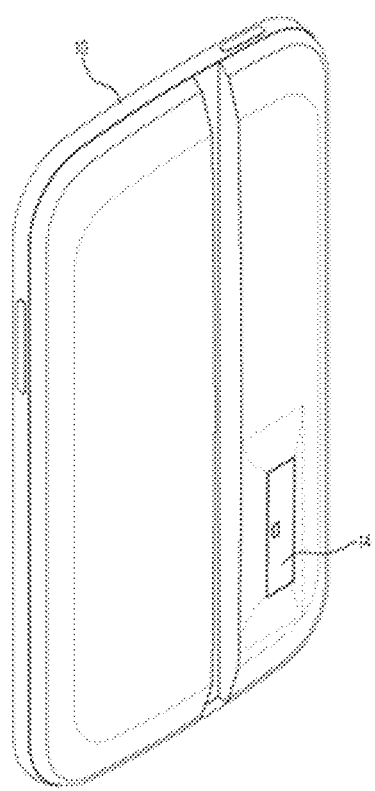
FIG. 6 is a rear side view of the main body of the portable diagnostic test apparatus of FIG. 1, in accordance with an exemplary embodiment.

FIG. 5 is a front view of a main body of the portable diagnostic test apparatus of FIG. 1, in accordance with an exemplary embodiment, and FIG. 6 is a rear side view of the main body of the portable diagnostic test apparatus of FIG. 1, in accordance with an exemplary embodiment.

The main body 10 may include the display unit 12 installed on the front side of the main body 10, as described with reference to FIGS. 1 and 2. In accordance with an exemplary embodiment, the display unit 12 formed on the main body 10 may be implemented as a touch screen unit 13 that uses a touch screen panel, as illustrated in FIG. 5.

If a touch unit, for example, a finger of the human body or a touch pen, touches a surface of the touch screen unit 13, the touch screen unit 13 generates a predetermined electrical signal according to a contact position and transmits the generated electrical signal to the central processing unit so that the portable diagnostic test apparatus 1 can perform a predetermined function. The touch screen unit 13 may be implemented with a predetermined touch screen panel, and the touch screen panel may use a capacitive touch screen method using an electrostatic capacity coupling effect or a resistive touch screen method, whereby pressure applied to the surface of a touch screen is sensed. Also, the touch screen panel may use an optical touch screen method using an optical sensor.

The touch screen unit 13 may be configured to display the various buttons 111 through 114 illustrated in FIGS. 1 and 2 in the form of predetermined icons 131 through 134 on the screen, as illustrated in FIG. 5. The user may touch various icons 131 through 134 displayed on the screen to control the portable diagnostic test apparatus 1 to eject at least one strip or to input various instructions or commands to be used for diagnosis.

Referring to FIG. 6, the main body 10 may include at least one strip keeping zone 14 that is formed on a rear side of the main body 10. At least one strip keeping portion 15 may be installed in the strip keeping zone 14. In detail, a space in which the strip keeping portion 15 may be installed, and a fixing unit for fixing the strip keeping portion 15 in place, may be disposed in the strip keeping zone 14. An insertion hole may be formed in the strip keeping zone 14 in accordance with exemplary embodiments. The insertion hole may be sealed by a cover. The insertion hole may be connected to an internal space of the strip keeping portion 15. The user may insert at least one strip 30 through the insertion hole and may enable the at least one strip 30 to be mounted in the internal space of the strip keeping portion 15. Thus, the user may replenish a strip in the strip keeping portion 15.

Hereinafter, the strip keeping portion 15 will be described with reference to FIGS. 7 through 13.

Figure 7:
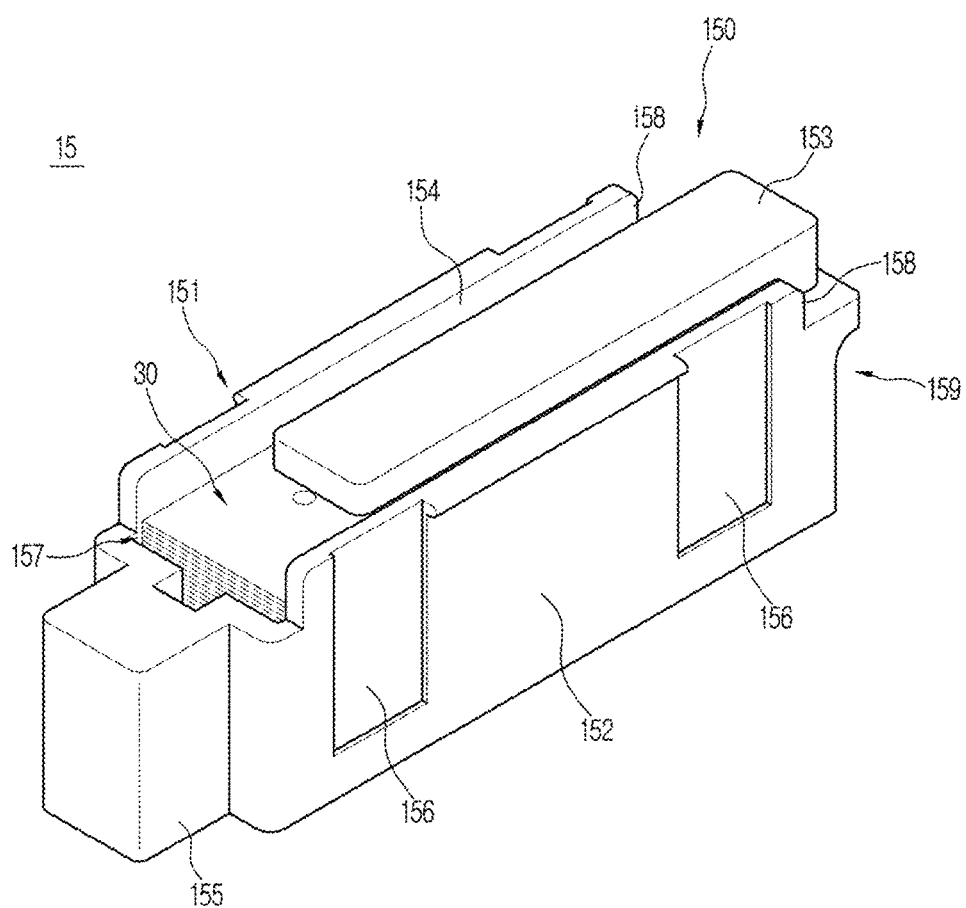
FIG. 7 is a view illustrating a housing of a strip keeping portion, in accordance with an exemplary embodiment.

FIG. 7 is a perspective view illustrating a housing and discharge portion of a strip keeping portion, in accordance with an exemplary embodiment. Hereinafter, according to an exemplary embodiment, a portion of FIG. 7 in which a stand 153 is formed is referred to as a lower part of the strip keeping portion, and portions in which a plurality of outer walls 151, 152, 155, and 159 are formed, are referred to as side surfaces of the strip keeping portion.

As illustrated in FIG. 7, the strip keeping portion 15 may include a housing 150 on which at least one strip may be stacked on an inner side of the housing 150.

In accordance with an exemplary embodiment, the housing 150 of the strip keeping portion 15 may include the plurality of outer walls 151, 152, 155, and 159 that are formed on side surfaces of the strip keeping portion 15, and the plurality of outer walls 151, 152, 155, and 159 may be connected to each other, thereby constituting a predetermined shape, for example, a box shape. A predetermined internal space may be formed at inner sides of the plurality of outer walls 151, 152, 155, and 159, and at least one strip 30 may be stacked on the predetermined internal space.

The strip keeping portion 15 may further include a discharge portion 157 through which at least one strip 30 may be discharged. The discharge portion 157 may be formed on at least one of the plurality of outer walls 151, 152, 155, and 159.

In accordance with an exemplary embodiment, heights of the outer walls 151 and 152 and 155 and 159 that face each other among the plurality of outer walls 151, 152, 155, and 159 may be the same, and heights of the outer walls that do not face each other among the plurality of outer walls 151, 152, 155, and 159 may be different. In this case, a height of at least one outer wall (for example, 155) among the plurality of outer walls 151, 152, 155, and 159 is smaller than heights of the other outer walls 151, 152, and 159 so that at least one strip may be discharged to the outside through a top end of at least one outer wall 155 having a small height. In this case, the top end of at least one outer wall 155 having the small height may be used as the discharge portion 157.

Of course, although not shown, a discharge hole formed in at least one outer wall among the plurality of outer walls 151, 152, 155, and 159 may be used as the discharge portion 157 through which at least one strip 30 may be discharged.

Coupling portions 156 that may be fixed and coupled to the outside, for example, to the strip keeping zone 14, may be formed on the plurality of outer walls 151, 152, 155, and 159. The coupling portions 156 may be formed in the shape of mounting grooves, as illustrated in FIG. 7. However, exemplary embodiments are not limited thereto. For example, the coupling portions 156 may have the shape of protrusions that protrude toward the plurality of outer walls 151, 152, 155, and 159.

The stand 153 on which stacked strips are supported may be formed on a lower part of the housing 150. The stand 153 may prevent at least one strip stacked on the housing 150 to be discharged in a direction in which the stand 153 is installed.

The stand 153 may be installed on the housing 150 so as to be spaced apart from the plurality of outer walls 151, 152, 155, and 159 by a predetermined gap, as illustrated in FIG. 7. In this case, a distance between the plurality of outer walls 151, 152, 155, and 159 and the stand 153 may be used as a guide portion 154 that guides movement of a first movement portion 161. An insertion portion 158 may be formed on one end of the guide portion 154 so that the first movement portion 161 may be inserted into the insertion portion 158 and may be movable along the guide portion 154.

An upper part of the housing 150 may be open. In this case, a user, e.g., a designer or manufacturer of the portable diagnostic test apparatus 1, may enable at least one strip 30 to be inserted through the open upper part of the housing 150.

FIG. 7 illustrates an example in which the housing 150 has a rectangular box shape. However, the shape of the housing 150 is not limited thereto, and the housing 150 may have various shapes, such as a circular shape, an oval shape, and a diamond shape. In this case, the entire shape of the housing 150 may be determined according to the shape or arrangement shape of each of the plurality of outer walls 151, 152, 155, and 159.

Figure 8:
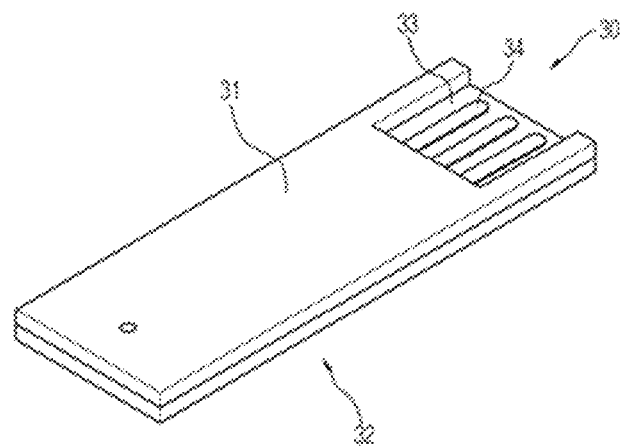
FIG. 8 is a perspective view of a strip in accordance with an exemplary embodiment.

FIG. 8 illustrates an exemplary embodiment of a strip.

The strip 30 may react with the blood of an object to be inspected, such as a human being or an animal, may convert the concentration of the blood content to be inspected in the blood, for example, blood sugar, blood cholesterol concentration, or neutral fat concentration into a predetermined electrical signal according to concentration, and may output the predetermined electrical signal. In detail, the strip 30 may convert bio-signals or a recognition reaction generated when analyzing a biological material into electrical signals using various methods, such as an electrochemical measurement method, photometry, and electrons, and may output the electrical signals.

The strip 30 may be a strip using the electrochemical measurement method, a strip using photometry, or a strip using enzymes, for example.

The type of the strip 30 may vary according to an object to be measured. For example, if blood sugar is to be measured, a strip using the electrochemical measurement method may be used. If cholesterol is to be measured, a strip using photometry or a strip using enzymes may be used.

As illustrated in FIG. 8, the strip 30 may have a shape in which an upper plate 31 and a lower plate 32 are stacked and adhered to each other, according to an exemplary embodiment.

If the strip 30 is a strip configured to use the electrochemical measurement method, a cutting portion 33 that is cut to a predetermined size may be formed in one end of the upper plate 31. A first electrode 34 may be formed on one end of the lower plate 32, and the first electrode 34 may be exposed to the outside through the cutting portion 33.

If blood is injected into the strip 30, the strip 30 may output a predetermined electrical signal according to blood sugar or cholesterol concentration in the blood, and the output electrical signal may be transferred to the outside, in particular, to the main body 10 through the first electrode 34. Then, the main body 10 may analyze blood sugar or cholesterol concentration in the blood according to the transmitted electrical signal and may control the display unit 12 to display the result of analysis.

If the strip 30 is a strip using photometry, a reaction portion that reacts according to glucose or red blood cells in the blood, instead of the above-described electrode 34, may be formed on the above-described strip 30. When photometry is used, the reaction portion may be formed between the upper plate 31 and the lower plate 32 or at an outer side of the upper plate 31 or the lower plate 32.

When photometry is used, a change in color of the reaction portion caused by various elements in the blood injected into the strip may be sensed, and a predetermined signal may be output and transmitted to the main body 10 according to the sensed result. The main body 10 may analyze the concentration of glucose in the blood based on the signal output as described above and may control the display unit 12 to display the result of analysis.

Figure 9:
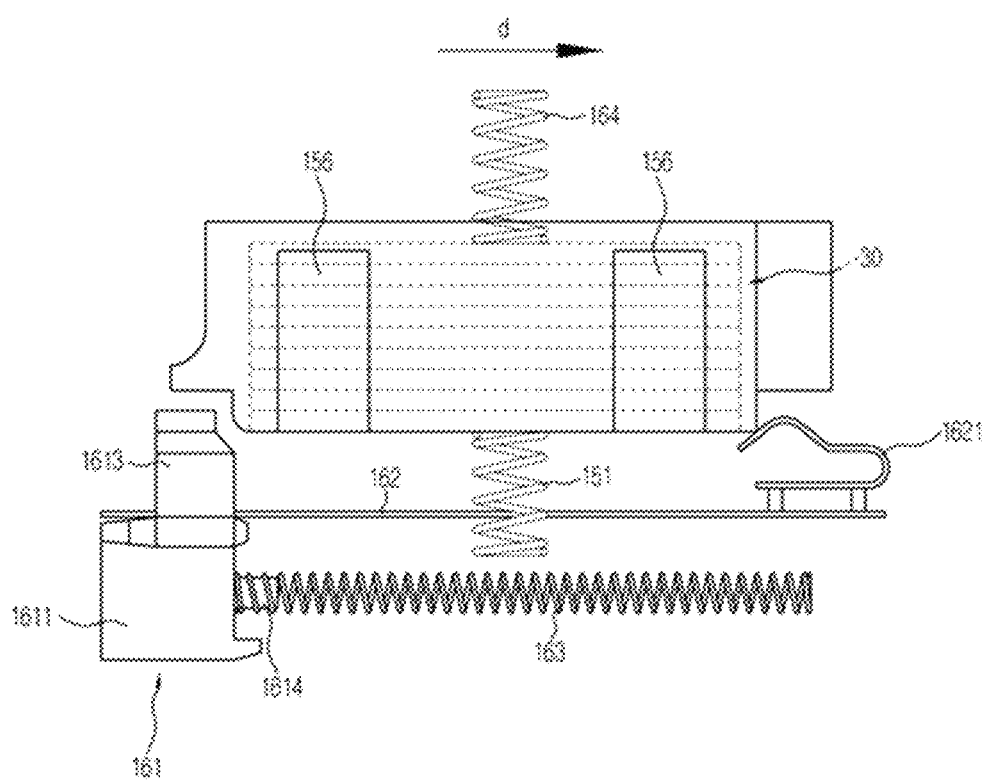
FIGS. 9 and 10 are views illustrating a strip keeping portion in accordance with an exemplary embodiment.
Figure 10:
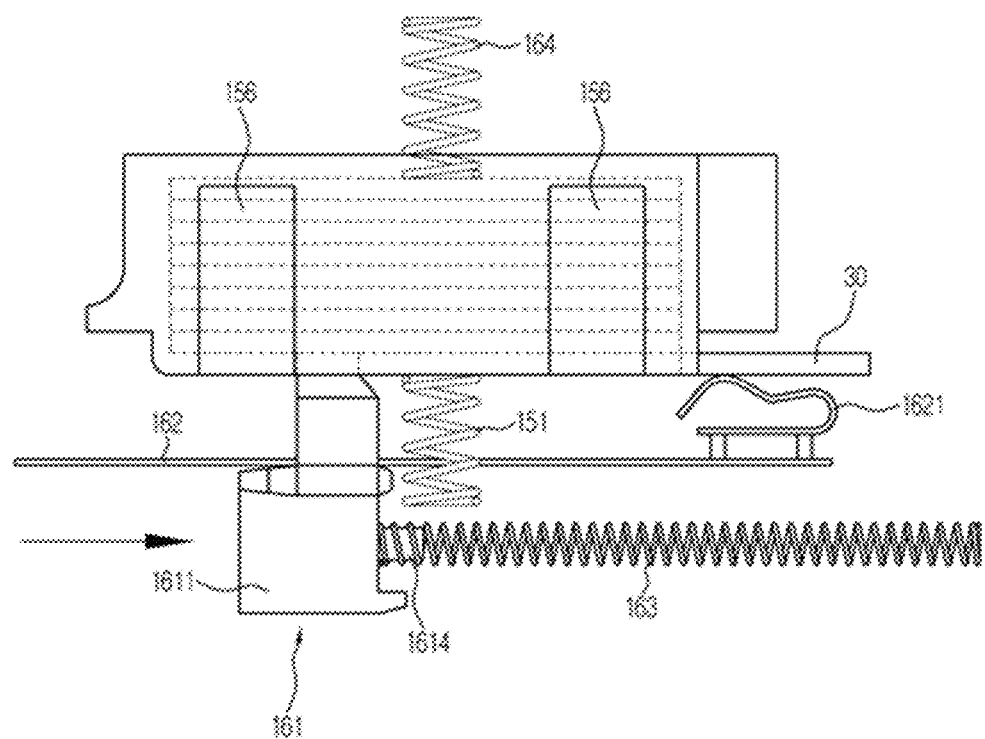

FIGS. 9 and 10 are views illustrating a strip keeping portion in accordance with an exemplary embodiment.

As illustrated in FIG. 9, the strip keeping portion 15 may further include the first movement portion 161, a guide bar 162, an elastic body 163 connected to the first movement portion 161, a second electrode 1621, and second movement portion 164, as well as the housing 150.

The first movement portion 161 may cause at least one strip disposed in the housing 150 to be discharged through the discharge portion 157. In detail, the first movement portion 161 may move at least one strip 30 to the discharge portion 157 while moving and pushing the at least one strip 30 stacked on the housing 150 so that the at least one strip 30 can be discharged to the outside through the discharge portion 157.

Also, the first movement portion 161 may push and discharge one among at least one strip 30 stacked on the housing 150 toward the discharge portion 157. In this case, the first movement portion 161 may push and discharge the at least one strip 30 toward the discharge portion 157 in a stacked order.

In detail, the first movement portion 161 may include a movement portion body 1611, at least one protrusion portion 1613 that protrudes from the movement portion body 1611 in a direction of the housing 150, and an elastic body connector 1614 to which the elastic body 163 may be connected.

The movement portion body 1611 may move according to external power that operates due to external manipulation, for example, pressing manipulation of the ejection button 111 by the user. The movement portion body 1611 may also move through the user's direct manual manipulation. The movement portion body 1611 may move in a right direction d of the drawing, e.g., in a direction of the discharge portion 157 of the housing 150, as illustrated in FIG. 10. In accordance with an exemplary embodiment, the movement portion body 1611 may move along the guide bar 162 that is separately formed.

The protrusion portion 1613 may move according to movement of the movement portion body 1611, may be inserted into the housing 150 through at least one movement portion insertion hole 158 and may move along at least one guide portion 154. The protrusion portion 1613 may move along the at least one guide portion 154, may push at least one of the strips 30 inside the housing 150 and may move the at least one strip 30 in a direction of the discharge portion 157, i.e., in the right direction d of FIG. 9. As a result, the strip 30 inside the housing 150 moves due to a pushing force of the protrusion portion 1613 and may be discharged to the outside of the housing 150 through the discharge portion 157.

In accordance with an exemplary embodiment, the protrusion portion 1613 may push only a strip disposed on the uppermost end or the lowermost end of at least one strip 30 stacked on the housing 150 and may also push only the strip disposed on the uppermost end or the lowermost end toward the discharge portion 157. For example, the protrusion portion 1613 may push only the strip 30 held directly in contact with the stand 153 of the housing 150 or disposed closest to the stand 153 to be discharged toward the discharge portion 157.

In accordance with an exemplary embodiment, the protrusion portion 1613 may push a plurality of strips 30 and may push the plurality of strips 30 toward the discharge portion 157.

The elastic body connector 1614 may connect the elastic body 163 that provides an elastic force for moving the first movement portion 161 or for returning to its original position and the first movement portion 161 so that the first movement portion 161 can move or can return to its original position according to the elastic force. In FIG. 9, the elastic body connector 1614 is disposed to extend along the movement direction d of the first movement portion 161, but is not limited thereto, and may be disposed in an opposite direction or some other direction.

The guide bar 162 may guide the movement portion body 1611 so that the movement portion body 1611 can uniformly move in an appropriate direction.

The elastic body 163 may be connected to the first movement portion 161 via the elastic body connector 1614 and may provide an elastic force to the first movement portion 161 so that the first movement portion 161 can move or can return to its original position.

For example, as illustrated in FIG. 10, it is assumed that the first movement portion 161 moves in a predetermined direction d according to external power or manual manipulation of the user. In this case, when the supply of external power to the first movement portion 161 is cut off or the user stops manually supplying the force applied to the first movement portion 161, the first movement portion 161 may be restored to its original position according to the elastic force of the elastic body 163, as illustrated in FIG. 9.

The elastic body 163 may be a spring, as illustrated in FIGS. 9 and 10, although is not limited thereto, and various types of members each having an elastic force, for example, an elastic body formed of a rubber material, may alternatively be used as the above-described elastic body 163.

The second electrode 1621 may be installed in the direction of the discharge portion 157, as illustrated in FIGS. 9 and 10. When the strip 30 is discharged through the discharge portion 157, the second electrode 1621 may contact the first electrode 34 formed on one end of the strip 30 and may receive an electrical signal output from the first electrode 34. The second electrode 1621 may be formed of a metal material and may have a predetermined elastic force.

From an outward appearance, the second electrode 1621 may have a bent shape in which a portion of the second electrode 1621 protrudes upwards, as illustrated in FIGS. 9 and 10. The second electrode 1621 is shaped to have the bent shape and thus may be further bent in a downward direction of the drawing, as illustrated in FIG. 10, when the strip 30 moves according to movement of the first movement portion 161. If the cutting portion 33 of the upper plate 31 of the strip 30 reaches a position of the second electrode 1621, the second electrode 1621 may be restored in an upward direction of the drawing according to the elastic force. As a result, the second electrode 1621 may contact the first electrode 34 and thus the second electrode 1621 may receive an electrical signal transmitted from the first electrode 34.

The second movement portion 164 may move at least one strip inside the housing 150 downwards or upwards.

In particular, when the first movement portion 161 discharges the strip 30 inside the housing 150 to the outside, the second movement portion 164 may move the strip 30 within the housing 150 so that the first movement portion 161 can discharge a new strip 30 to the outside. The moving strip 30 may be held on the above-described stand 153, may be pushed by the protrusion portion 1613 of the first movement portion 161, and may be discharged to the outside again. In this case, the second movement portion 164 may move the strip 30 by a predetermined distance due to the elastic force of the second movement portion, so that the strip 30 may be disposed in a predetermined position.

Although not shown, in accordance with another exemplary embodiment of the strip keeping portion 15, the strip keeping portion 15 may further include an optical signal measurement module for sensing a change in color formation of the strip 30 according to a reagent reaction. As described above, the optical signal measurement module may include a light source and a sensing unit. The light source and the sensing unit may be installed inside or outside the above-described housing 150.

The exemplary embodiments illustrated in FIGS. 9 and 10 may be applied to the strip keeping portion 15, and an exemplary embodiment using the optical signal measurement module may be applied to the strip keeping portion 15. Also, the above-described exemplary embodiments may be applied to the strip keeping portion 15. When the above-described exemplary embodiments are applied to the strip keeping portion 15, the above-described exemplary embodiments may be selectively used by the user or according to predetermined settings.

The strip keeping portion 15 described above may be disposed in the main body 10 or the accommodation portion 20 according to an exemplary embodiment.

Figure 11:
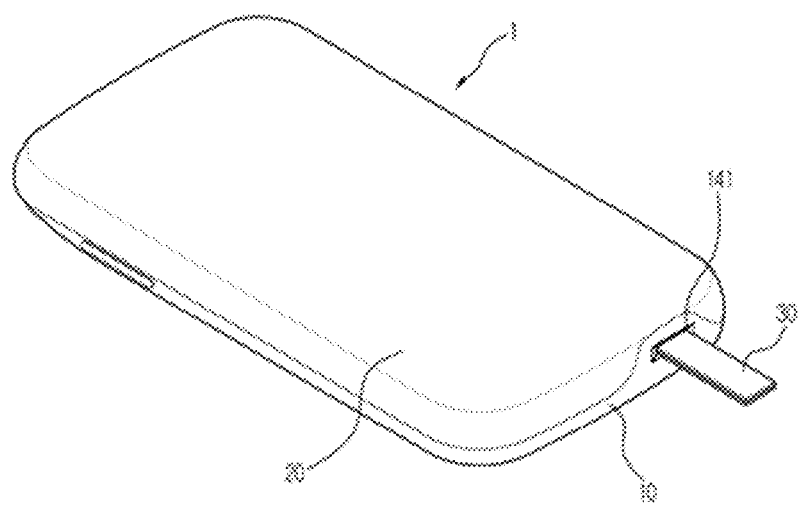
FIG. 11 is a view illustrating ejecting of the strip of the portable diagnostic test apparatus of FIG. 1.

FIG. 11 is a view illustrating ejecting of the strip of the portable diagnostic test apparatus of FIG. 1.

The strip keeping portion 15 described above may include the first movement portion 161 which is configured to move according to the user's manipulation of the ejection button 111 and to discharge at least one strip 30. This procedure may be automatically performed. The discharged strip 30 is ejected through the outlet 141 formed in the main body 10 or the accommodation portion 20 of the portable diagnostic test apparatus 1. As a result, when the user manipulates the above-described ejection button 111 by pressing the ejection button 111, the strip keeping portion 15 may automatically discharge at least one strip 30 to the outside of the portable diagnostic test apparatus 1 so that the user can measure blood sugar using the strip 30.

The user can drop a predetermined amount of blood onto the ejected strip 30 so as to measure blood sugar or blood cholesterol concentration. Thus, the user can easily measure blood sugar, cholesterol, or neutral fats using the strip 30.

Hereinafter, the accommodation portion 20 of the portable diagnostic test apparatus 1 will be described with reference to FIGS. 12 and 13.

Figure 12:
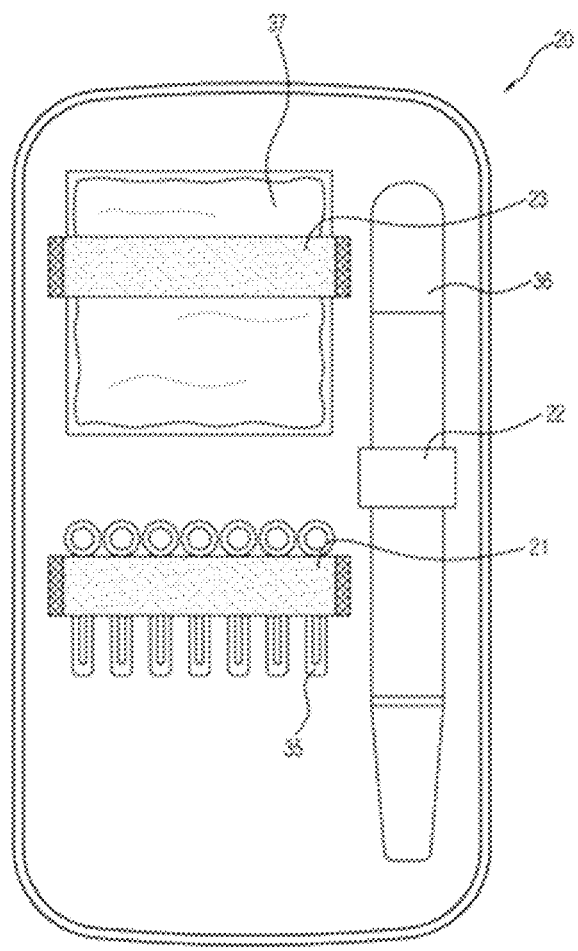
FIG. 12 is a front view of an accommodation portion of the portable diagnostic test apparatus of FIG. 1, in accordance with an exemplary embodiment.

FIG. 12 is a front view of an accommodation portion of the portable diagnostic test apparatus of FIG. 1, in accordance with an exemplary embodiment.

In accordance with an exemplary embodiment, an accommodation space which accommodates various types of instruments, such as, for example, instruments to be used for drawing blood and making a diagnosis, may be formed in the accommodation portion 20.

The accommodation space may include at least one of a blood drawing needle accommodation portion 21, a blood drawing device accommodation portion 22, and an alcohol cotton accommodation portion 23, as illustrated in FIG. 12.

The blood drawing needle accommodation portion 21 may accommodate at least one blood drawing needle 35.

The blood drawing needle 35 makes a wound in the skin of an object to be inspected, such as a human body, so that blood can be discharged to the outside through the wound part. The blood drawing needle accommodation portion 21 may include a strap in which at least one blood drawing needle 35 is fixed, and a blood drawing needle mounting portion on which at least one blood drawing needle 35 is mounted. According to an exemplary embodiment, the strap may be a band having a predetermined elastic force. The blood drawing needle mounting portion may be a mounting groove. The strap and the blood drawing needle mounting portion may provide a function of fixing a blood drawing needle to be stably disposed in a predetermined position within the accommodation portion 20.

The blood drawing device accommodation portion 22 may accommodate at least one blood drawing device.

According to an exemplary embodiment, the term blood drawing device refers to an instrument having a small window structure and which is configured to be used for the purpose of drawing blood. Although not shown, the blood drawing device may include a cylindrical body and a cap that covers one end of the body. A blood drawing needle insertion groove, into which the blood drawing needle may be coupled and fixed, may be formed in one end of the body covered by the cap. The user may fix the blood drawing needle at one end of the body of the drawing blood device and may couple the cap to the body and then may make a wound in a part of the human body, for example, in a finger, using the blood drawing needle that protrudes to the outside through a hole formed in one end of the cap so as to perform the operation of drawing blood.

The blood drawing device accommodation portion 22 may include at least one strap formed in a ring shape so as to accommodate the blood drawing device, as illustrated in FIG. 12. The ring-shaped strap may have a predetermined elastic force, and the blood drawing device inserted between rings may be fixed according to the elastic force.

The alcohol cotton swab accommodation portion 23 may provide a function of accommodating an alcohol cotton swab 37. The alcohol cotton accommodation portion 23 may include a strap in which at least one piece of an alcohol cotton swab 37 is fixed, and an alcohol cotton mounting portion on which the at least one piece of the alcohol cotton swab 37 is mounted, similar to the blood drawing needle accommodation portion 21 described above.

Figure 13:
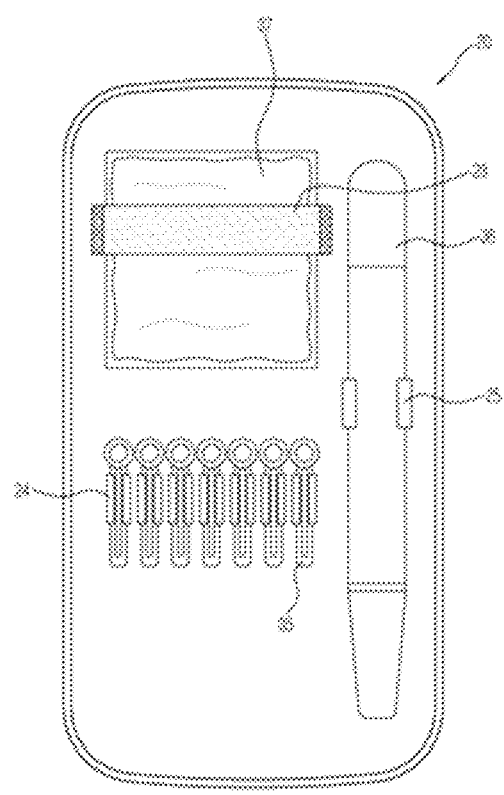
FIG. 13 is a front view of an accommodation portion of the portable diagnostic test apparatus of FIG. 1, in accordance with another exemplary embodiment.

FIG. 13 is a front view of an accommodation portion of the portable diagnostic test apparatus 1 of FIG. 1, in accordance with another exemplary embodiment.

In accordance with another exemplary embodiment of the accommodation portion 20 of the portable diagnostic test apparatus 1 of FIG. 1, a blood drawing needle accommodation portion 24 may include at least one fixing hook that may fix at least one blood drawing needle 35, as illustrated in FIG. 13. The blood drawing needle 35 may be inserted and fixed to the fixing hook and may be accommodated in the accommodation portion 20.

In the same way, a blood drawing device accommodation portion 25 may also include at least one fixing hook that may fix at least one blood drawing device 36. At least one blood drawing device may be inserted and fixed to the fixing hook and may be accommodated in the accommodation portion 20.

FIGS. 12 and 13 illustrate exemplary embodiments in which the blood drawing needle accommodation portions 21 and 24 and the blood drawing device accommodation portions 22 and 25 of the accommodation portion 20 fix the blood drawing needle 35 and the blood drawing device 36 in the same manner. However, the blood drawing needle accommodation portions 21 and 24 and the blood drawing device accommodation portions 22 and 25 do not necessarily need to fix the blood drawing needle 35 and the blood drawing device 36 in the same manner. For example, an exemplary embodiment may combine the blood drawing needle accommodation portion 21 which uses a strap, as illustrated in FIG. 12, and the blood drawing device accommodation portion 25 which uses a predetermined fixing hook, as illustrated in FIG. 13.

The above-described accommodation portion 20 may be formed of a solid material, such as one of various types of metals, or a material having an elastic force, such as one of various types of resins or rubbers.

Hereinafter, various exemplary embodiments of the portable diagnostic test apparatus 1 including the main body 10 and the accommodation portion 20 will be described with reference to FIGS. 14 through 19.

Figure 14:
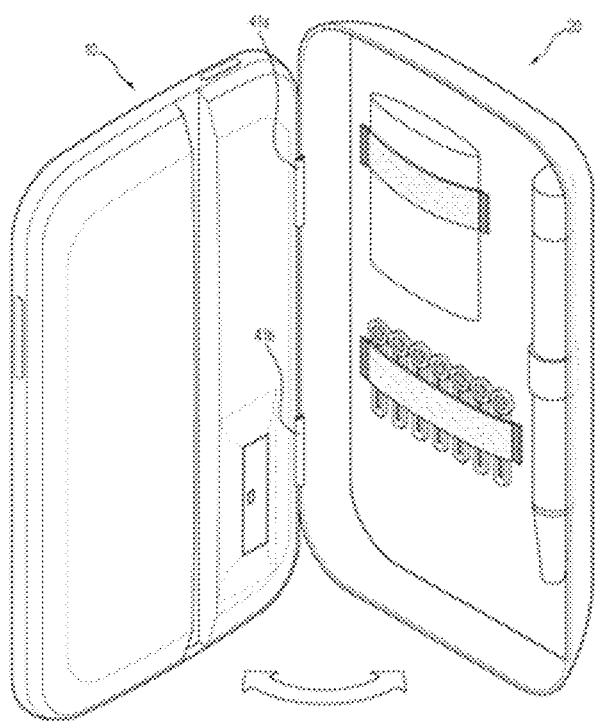
FIG. 14 is a view illustrating a portable diagnostic test apparatus in which a main body and an accommodation portion are hinge-coupled to each other, in accordance with an exemplary embodiment.

FIG. 14 is a view illustrating a portable diagnostic test apparatus in which a main body and an accommodation portion are hinge-coupled to each other, in accordance with an exemplary embodiment.

As illustrated in FIG. 14, in accordance with an exemplary embodiment, the main body 10 and the accommodation portion 20 may be coupled to each other using at least one hinge 41a and 41b. The main body 10 and the accommodation portion 20 may be rotated relative to each other by at least one hinge 41a and 41b, and the accommodation portion 20 may be opened and closed according to the rotation of the main body 10 and/or the accommodation portion 20.

A fastening hole may be provided on an opposite side to a side in which hinges of the main body 10 and the accommodation portion 20 are installed, so as to prevent the main body 10 and the accommodation portion 20 from inadvertently opening contrary to a user's intention, according to an exemplary embodiment.

Figure 15:
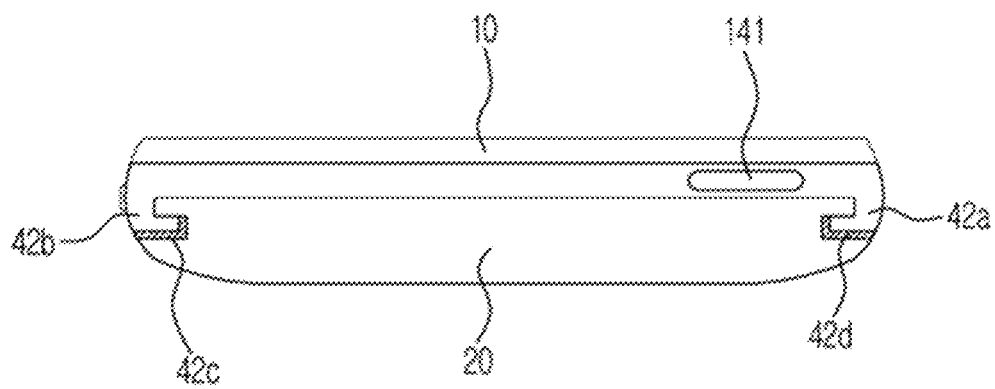
FIGS. 15 and 16 are views illustrating a portable diagnostic test apparatus in which a main body and an accommodation portion are coupled to each other by sliding, in accordance with an exemplary embodiment.
Figure 16:
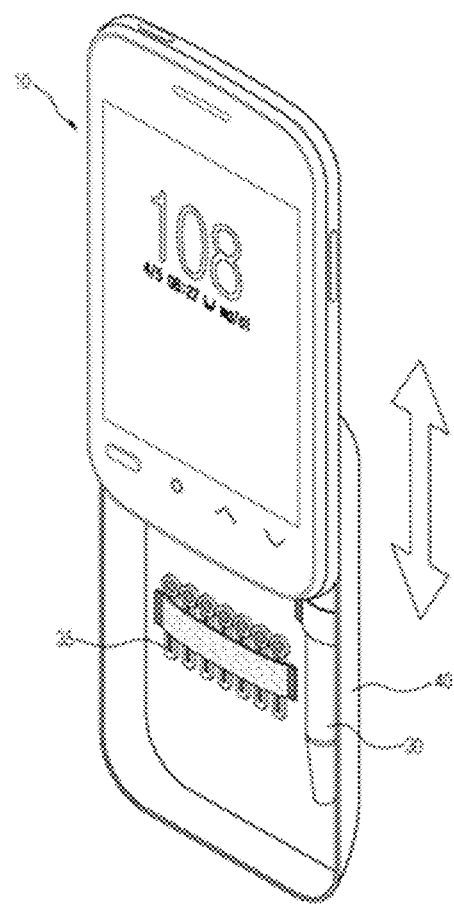

FIGS. 15 and 16 are views illustrating a portable diagnostic test apparatus in which a main body and an accommodation portion are coupled to each other by sliding, in accordance with an exemplary embodiment.

As illustrated in FIGS. 15 and 16, the main body 10 and the accommodation portion 20 may be coupled to each other by sliding and may slide relative to each other. In this case, at least one of the main body 10 and the accommodation portion 20 may move in a predetermined direction to thereby open and close the accommodation portion 20, as illustrated in FIG. 15.

In detail, for example, as illustrated in FIG. 16, sliding members 42a and 42b may be provided on at least one of the main body 10 and the accommodation portion 20, and sliding rails 42c and 42d may be provided on the other accommodation portion 20 or main body 10 in which no sliding members 42a and 42b are formed. In this case, the sliding members 42a and 42b may move along the sliding rails 42c and 42d. Although not shown, the sliding members 42a and 42b may include sliding wheels that roll along the sliding rails 42c and 42d.

Figure 17:
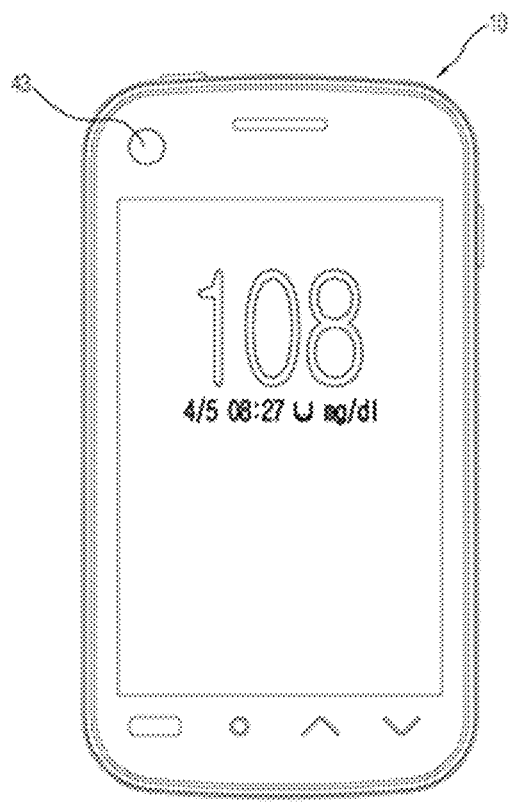
FIGS. 17 and 18 are views illustrating a portable diagnostic test apparatus in which a main body and an accommodation portion are coupled to each other via a pivot member, in accordance with an exemplary embodiment.
Figure 18:
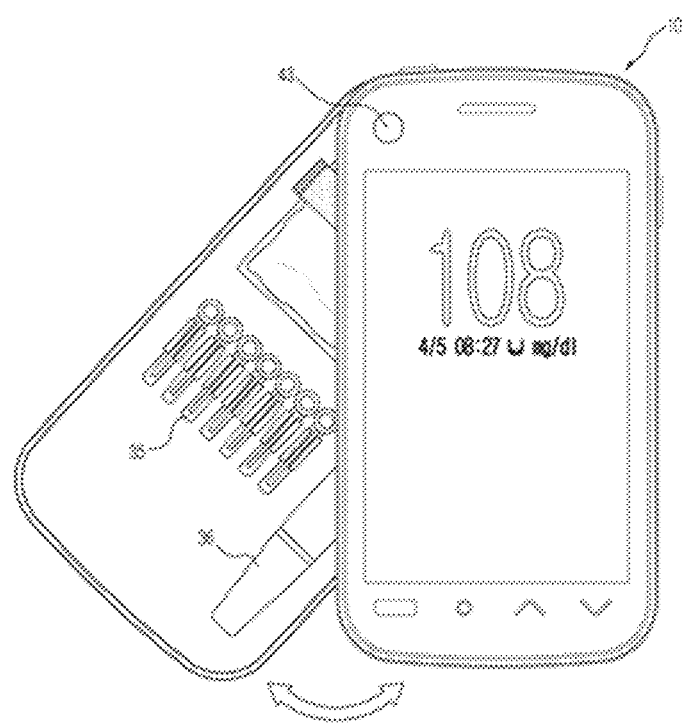

FIGS. 17 and 18 are views illustrating a portable diagnostic test apparatus in which a main body and an accommodation portion are coupled to each other via a pivot member, in accordance with an exemplary embodiment.

As illustrated in FIGS. 17 and 18, a pivot member 43 may be installed at a portion of the main body 10 and the accommodation portion 20. The pivot member 43 may be installed at both the main body 10 and the accommodation portion 20 so that the main body 10 and the accommodation portion 20 may be rotated around the pivot member 43. As a result, as illustrated in FIG. 18, the accommodation portion 20 may be opened and closed according to at least one rotation of the main body 10 and the accommodation portion 20.

Hereinafter, an example of a method of using the portable diagnostic test apparatus of FIG. 1 will be described with reference to FIGS. 19 through 21.

Figure 19:
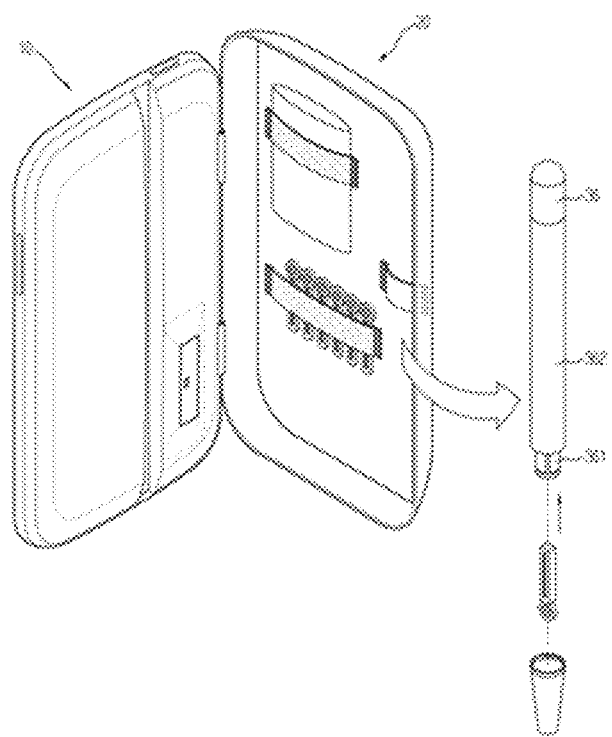
FIGS. 19 through 21 are views illustrating an example of a method of using the portable diagnostic test apparatus.
Figure 20:
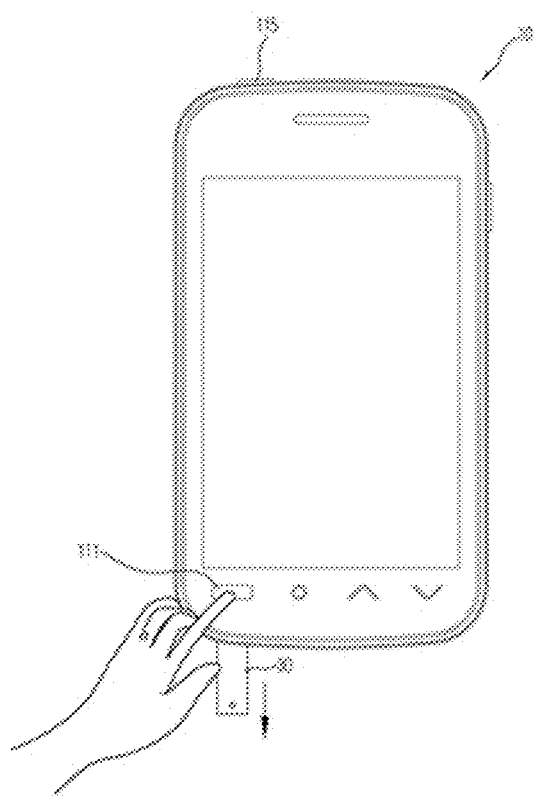
Figure 21:
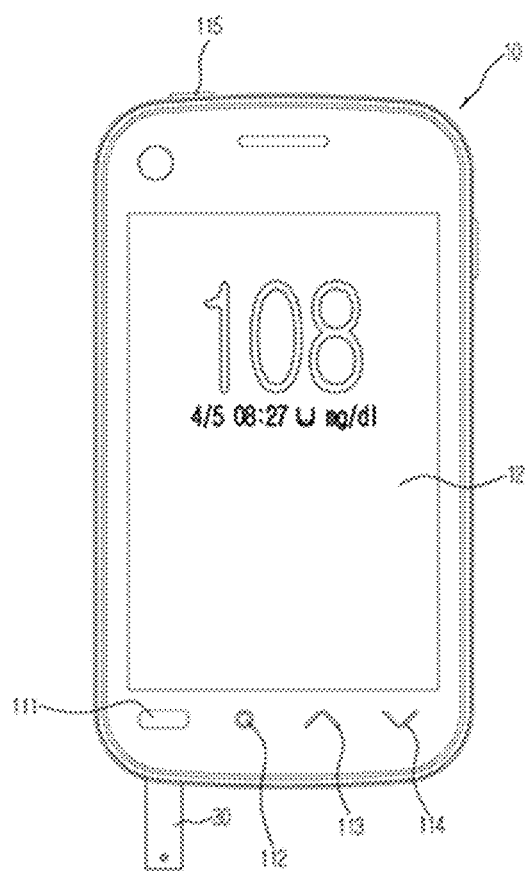

FIGS. 19 through 21 are views illustrating an example of a method of using the portable diagnostic test apparatus of FIG. 1.

As illustrated in FIG. 19, when the portable diagnostic test apparatus 1 includes the main body 10 and the accommodation portion 20 that are hinge-coupled to each other, the user may rotate at least one of the main body 10 or the accommodation portion 20 of the portable diagnostic test apparatus 1 around a hinge shaft, thereby opening the accommodation portion 20. The user may take out the blood drawing needle 35 and the blood drawing device 36 disposed in the accommodation space of the accommodation portion 20, separate a cap 361 of the blood drawing device 36 from a blood drawing device body 362, insert and fix the blood drawing needle 35 into one end of the blood drawing device body 362, and couple the blood drawing device body 362 and the blood drawing needle 35. The user may then couple the cap 361 to one end of the drawing blood device body 362, and cause the blood drawing needle 35 to protrude toward the outside through a hole formed in an end of the cap 361 by manipulating the drawing blood device 36. Then, a wound may be made in the human body, e.g., in a finger, by the protruding blood drawing needle 35, and blood ejected from the wound may be collected.

Subsequently, as illustrated in FIG. 20, the user presses the ejection button 111 formed on an outer side of the portable diagnostic test apparatus 1 after drawing blood (although it is understood that this operation could also be performed before drawing blood), and the strip 30 is ejected through the outlet 141 in an electronic or mechanical manner according to pressing the ejection button 111. The user coats the collected blood on the ejected strip 30.

Then, the portable diagnostic test apparatus 1 measures blood sugar, blood cholesterol concentration, neutral fat concentration, or blood alcohol concentration based on the blood coated on the strip 30 and displays a result of measurement on the display unit 12, as illustrated in FIG. 21. As a result, the user can simply measure blood sugar, blood cholesterol concentration, neutral fat concentration, or blood alcohol concentration and can perform self-diagnosis.

The used strip 30 may be removed from the portable diagnostic test apparatus 1 after being used. In this case, the user may manually take out the strip 30 from the outlet 141 so as to remove the used strip 30 from the portable diagnostic test apparatus 1. Also, the strip 30 may be discharged to an outside of the outlet 141 using a strip ejector installed on the portable diagnostic test apparatus 1 so as to remove the strip 30 from the portable diagnostic test apparatus 1.

As described above, in accordance with the above-described diagnostic test apparatus according to exemplary embodiments, a user can easily and conveniently use and keep the diagnostic test apparatus. Also, the user can conveniently carry the diagnostic test apparatus.

In accordance with the above-described diagnostic test apparatus according to exemplary embodiments, various instruments to be used for drawing blood and diagnosis, such as an electronic device for diagnosis, a strip, a blood drawing device, a blood drawing needle, and an alcohol cotton swab (e.g., made of wool), can be easily kept and carried so that users, e.g., patients or medical professionals, can easily diagnose and measure blood sugar using various instruments whenever the patients need.

Also, in accordance with the above-described diagnostic test apparatus according to exemplary embodiments, users can simply measure blood sugar, cholesterol, or neutral fats so that the users can easily perform self-diagnosis in a hospital, a workplace, or a house.

In addition, in accordance with the above-described diagnostic test apparatus according to exemplary embodiments, various objects to be measured, such as blood sugar, cholesterol, and neutral fats, can be measured using one device so that the operation of making a diagnosis based on the various measured objects can also be performed.

Furthermore, in accordance with the above-described diagnostic test apparatus according to exemplary embodiments, a diabetes patient can discretely and enjoyably take a measurement of blood sugar and make a self-diagnosis even if the diabetes patient has poor eyesight, due to the small volume and esthetic appealing appearance of the diagnostic test apparatus, thereby promoting confidentiality of diabetes testing.

Although a few exemplary embodiments have been shown and described, it would be appreciated by those skilled in the art that changes may be made in these exemplary embodiments without departing from the principles and spirit of the invention, the scope of which is defined in the claims and their equivalents.

What is claimed is:

1. A portable diagnostic test apparatus comprising:
an accommodation portion comprising an outer side, an inner side, and an accommodation space provided on the inner side;
a hinge; and
a main body coupled to the accommodation portion by the hinge,
wherein the portable diagnostic test apparatus is configured to be opened and closed by rotating one of the accommodation portion and the main body about the hinge, and
wherein the main body is configured to obtain a result of a measurement based on data collected from drawn blood,
wherein the main body and/or the accommodation portion comprise at least one strip keeping portion configured to store at least one strip, and
wherein the at least one strip keeping portion comprises:
a housing configured to house a stack of a plurality of the at least one strips;
a discharge portion formed on at least one side surface of the housing and configured to sequentially discharge the plurality of the at least one strips; and
a first movement portion configured to move one of the plurality of the at least one strips to the discharge portion,
wherein the main body and/or the accommodation portion comprise at least one outlet through which the at least one strip is ejected when the at least one strip is discharged from the at least one strip keeping portion,
wherein the main body and/or the accommodation portion comprise an ejection button, the ejection button operating a sliding member abutting against the at least one strip, and the sliding member physically ejects the at least one strip from the accommodation portion through the at least one outlet, and
wherein the ejection button ejects at least one test strip from the strip keeping portion automatically, and the sliding member operated by the ejection button includes a deformable member which becomes compressed automatically in response to a push of the ejection button to physically move the at least one test strip through the at least one outlet.

2. The portable diagnostic test apparatus of claim 1, wherein the accommodation space comprises at least one of:
a blood drawing device accommodation portion configured to store at least one blood drawing device, and
a blood drawing needle accommodation portion configured to store at least one drawing needle.

3. The portable diagnostic test apparatus of claim 1, wherein the main body is configured to obtain a result of a measurement regarding at least one of blood sugar, cholesterol, and neutral fats based on the data collected from the drawn blood.

4. The portable diagnostic test apparatus of claim 1, wherein the main body is configured to obtain the result of the measurement using at least one of an electrochemical measurement method, an enzyme color reaction detection method, and a photometry method.

5. The portable diagnostic test apparatus of claim 1, wherein the main body comprises a display panel configured to display the result of the measurement.

6. The portable diagnostic test apparatus of claim 5, wherein the display panel comprises a touch screen panel.

7. The portable diagnostic test apparatus of claim 6, wherein the touch screen panel is configured to display a graphic user interface (GUI) for controlling the main body.

8. The portable diagnostic test apparatus of claim 1, further comprising at least one outlet provided on at least one of the main body and the accommodation portion, wherein each of the plurality of the at least one strips sequentially discharged through the discharge portion is configured to be ejected through the at least one outlet.

9. The portable diagnostic test apparatus of claim 1, wherein the first movement portion is configured to push the plurality of the at least one strips in a stacked order and is configured to move the plurality of the at least one strips to the discharge portion so that one of the plurality of the at least one strips is positioned to be discharged through the discharge portion.

10. The portable diagnostic test apparatus of claim 1, wherein the first movement portion is configured to push one strip among the plurality of the at least one strips stacked on the housing and is configured to move the one strip to the discharge portion so that the one strip is positioned to be discharged through the discharge portion.

11. The portable diagnostic test apparatus of claim 1, wherein the at least one strip keeping portion further comprises a second movement portion configured to move the plurality of the at least one strips inside the housing downwards or upwards after one of the at least one strips is discharged through the discharge portion.

12. The portable diagnostic test apparatus of claim 1, wherein the housing comprises a guide portion configured to guide movement of the first movement portion.

13. The portable diagnostic test apparatus of claim 1, wherein each of the plurality of the at least one strips respectively comprises a first electrode, and the at least one strip keeping portion further comprises at least one second electrode configured to contact the first electrodes.

14. The portable diagnostic test apparatus of claim 1, wherein the at least one strip keeping portion further comprises at least one elastic body configured to apply an elastic force to the first movement portion.

15. The apparatus of claim 11,
wherein the first movement portion comprises a first deformable member, and the second movement portion comprises a second deformable member in contact with the strip disposed at the uppermost end or lowermost end of test strips stacked in the housing, the second deformable member exerting a force on the strip at the uppermost end or the lowermost end, in a direction substantially perpendicular to a force exerted by the first movement portion on the test strip at the uppermost end or the lowermost end in the housing.

* * * * *